US006613749B1

(12) United States Patent
Forstováet al.

(10) Patent No.: US 6,613,749 B1
(45) Date of Patent: Sep. 2, 2003

(54) PAPOVAVIRUS PSEUDOCAPSIDS AND USE THEREOF FOR EXOGENOUS MATERIAL TRANSFER

(75) Inventors: Jitka Forstová, Prague (CZ); Beverly Elayne Griffin, London (GB); Nina Sheila Krauzewicz, Reading (GB)

(73) Assignee: Imperial College Innovations Limited, London (GB)

( * ) Notice: Subject to any disclaimer, the term of this patent is extended or adjusted under 35 U.S.C. 154(b) by 0 days.

(21) Appl. No.: 08/280,306

(22) Filed: Jul. 26, 1994

(51) Int. Cl.$^7$ .................. A61K 48/00; C12N 15/00; C12N 15/63
(52) U.S. Cl. .............. 514/44; 435/320.1; 435/69.1; 435/325; 435/91.4; 435/455
(58) Field of Search ............... 424/499; 435/235.1, 435/172.3, 240.2, 325, 69.1, 91.4, 455; 514/44; 536/23.1; 935/52, 54, 57

(56) References Cited

U.S. PATENT DOCUMENTS 5,437,951 A * 8/1995 Lowy et al. ............ 435/69.1
6,046,173 A * 4/2000 Forstová et al. ............ 514/44

OTHER PUBLICATIONS

JC Hanvey et al (1992) Science 258: 1481–1485.*
E Marshall (1995) Science 269: 1050–1055.*
KW Culver et al (1994) Trends in Genetics 10: 174–178.*
CP Hodgson (1995) Expert Opinion in Therapeutic Patents 5: 459–468.*
N Miller et al (1994) Parasitology Today 10: 92–97.*
RA Stull et al (1995) Pharmaceutical Research 12: 465–483.*
S Wu-Pong (1994) Pharmaceutical Technology 118: 102–114.*
RW Wagner (1994) Nature 372: 333–335.*
N Miller et al (1995) FASEB J 9: 190–199.*
Colomar, et al., "Opening And Refolding Of Simian Virus 40 And In Vitro Packaging Of Foreign DNA", *J. Virol.*, 67:2779–2786 (1993).
Cook, et al., "Gene Therapy For B–Cell Lymphoma In A SCID Mouse Model Using An Immunoglobullin–Regulated Diphtheria Toxin Gene Delivered", *Cancer–Biother*, 9(2):131–141 (1994).
Gharakanian, et al., "SV40 VP1 Assembles Into Disulfide–Linked Postpentameric Complexes In Cell–Free Lysates", Virology, 207(1):251–154 (1995).

Kirnbauer, et al., Papillomavirus L1 Major Capsid Protein Self–Assembles Into Virus–Like Particles That Are Highly Immunogenic, *Proc. Natl. Acad. Sci. USA*, 89:12180–12184 (1992).
Sahli, et al., "Defect In Entry And Altered Pathogenicity Of A Polyoma Virus Mutant Blocked In VP2 Myristylation", *Virol.*, 192:142–153 (1993).
Zhou, et al., "Interaction Of Human Papillomavirus (HPV) Type 16 Capsid Proteins With HPV DNA Requires An Intact L2 N–Terminal Sequence", *J. Virol.*, 68:619–625 (1994).
Barr, S.M., et al., "Cell–Free Assembly of a Polyoma–like Particle from Empty Capsids and DNA", *Virology*, 96:656–659 (1979).
Forstová , J., et al., "Cooperation of Structural Proteins During Late Events in the Life Cycle of Polyomavirus", *J. Virol.*, 67:1405–1413 (Mar., 1993).
Hagensee, M.E., et al., "Self–assembly of Human Papillomavirus Type 1 Capsids by Expression of the L1 Protein Alone or by Coexpression of the L1 and L2 Capsid Proteins", *J. Virol.*, 67:315–322 (Jan., 1993).
Haynes, J.I., et al., "Mutations in the Putative Calcium–binding Domain of Polyomavirus VP1 Affect Capsid Assembly", *J. Virol.*, 67:2486–2495 (May, 1993).
Montross, L., et al., "Nuclear Assembly of Polyomavirus Capsids in Insect Cells Expressing the major Capsid Protein VP1", *J. Virol.*, 65:4991–4998 (Sep., 1991).
Oppenheim, A., et al., "Efficient Introduction of Plasmid DNA Into Human Hemopoietic Cells by Encapsidation in Simian Virus 40 Pseudovirions", *Proc. Natl. Acad. Sci. USA*, 83:6925–6929 (Sep., 1986).
Sandig, V., et al., "Generation of DNA–packaging Proteins by Overexpression in the Baculovirus/insect Cell System", *12$^{th}$ Meeting of the European Society for Animal Cell Technology* (May, 1993).
Slilaty, S.N., et al., "Gene Transfer by Polyoma–Like Particles Assembled in a Cell–Free System", *Science*, 220:725–727 (1983).

* cited by examiner

*Primary Examiner*—Dave T. Nguyen
(74) *Attorney, Agent, or Firm*—Holland & Knight LLP (57) ABSTRACT

The present invention relates to biologically useful material in the form of a pseudocapsid formed from papovavirus major capsid antigen and excluding minor capsid antigens, which pseudocapsid incorporates exogenous material. The invention also relates to a method of using the pseudocapsids as vectors for exogenous material transfer, especially gene transfer in the therapy of genetic disorders, of other uses such as antibody or drug targeting.

19 Claims, 5 Drawing Sheets

PAPOVAVIRUS PSEUDOCAPSIDS AND USE THEREOF FOR EXOGENOUS MATERIAL TRANSFER

BACKGROUND OF THE INVENTION

1. Field of the Invention

The present invention relates to the packaging of material for delivery, for example in gene therapy and other situations.

2. Description of Related Art

Gene transfer, as a means to effect gene therapy, is becoming increasingly important. Numerous studies have been carried out that seek to harness the inherent ability of viruses to infect eukaryotic cells in order to introduce a selected gene into a suitable recipient host (as reviewed: Anderson, 1992; Morgan and Anderson, 1993; Mulligan, 1993). Adenoviruses have proved particularly attractive for this purpose in that their genome can be manipulated to incorporate up to about 8 kbp of foreign DNA and, unlike retroviral vectors, transduced genes, can be expressed in non-dividing cells. One particular handicap shared by all the present virus vectors, however, is that they introduce unwanted viral genetic information alongside the gene of interest into the recipient host. The disadvantages of this unwanted viral material remain to be determined fully, but there is a great need for means to carry out improved genetic transfer without introduction of unwanted viral genes into target cells.

Physical, non-viral gene transfer methods such as chemical and mechanical techniques and membrane fusion-mediated transfer via liposomes have been used (Morgan and Anderson, 1993). However, the efficiency of transfer, in terms of expression of the genetic material transferred, is low. In other words, these methods are inefficient at transferring genetic material into cells in a stable manner so that the material is biologically functional.

The empty capsids of papovaviruses such as the mouse polyoma virus have received attention as possible vectors for gene transfer.

Barr et al, 1979, first described the use of polyoma empty particles when polyoma DNA and purified empty capsids were incubated in a cell-free system. The DNA of the new particle was protected from the action of pancreatic DNase. Slilaty and Aposhian, 1983, describe the use of those reconstituted particles for transferring a transforming polyoma DNA fragment to rat FIII cells. The empty capsids and reconstituted particles consist of all three of the polyoma capsid antigens VP1, VP2 and VP3 and there is no suggestion that pseudocapsids consisting of only the major capsid antigen VP1, could be used in genetic transfer.

Montross et al. 1991, described only the major capsid antigen, the cloning of the polyoma virus VP1 gene and its expression in insect cells. Self-assembly of empty pseudocapsids consisting of VP1 is disclosed, and pseudocapsids are said not to contain DNA. It is also reported that DNA inhibits the in vitro assembly of VP1 into empty pseudocapsids, which suggests that said pseudocapsids could not be used to package exogenous DNA for transfer to host cells. The results of Sandig et al. 1993, showed that empty capsids incorporating exogenous DNA could transfer DNA in a biologically functional manner to host cells only if the particles consisted of all three polyoma capsid antigens VP1, VP2 and VP3. Pseudocapsids consisting of VP1 were said to be unable to transfer the exogenous DNA so that it could be expressed in the host cells. We now know that this was probably because $Ca^{2+}$ ions were not included in the medium in which the pseudocapsids were prepared. Haynes et al (1993) J. Virol., 67, 2486–2495) discuss the effect of calcium ions on empty VP1 pseudocapsid assembly. Hagensee et al (1993) J. Virol., 67, 315–322 disclosed the production of L1 and L1/L2 human papillomavirus capsids, but did not suggest their use to carry exogenous material.

BRIEF SUMMARY OF THE INVENTION

The present invention aims to overcome the above problems associated with known viral and non-viral methods of exogenous material transfer by providing a method involving the use of a pseudocapsid consisting of a papovavirus major capsid antigen to transfer exogenous material to a host cell wherein that material is biologically functional.

The invention also aims to provide a pseudocapsid suitable for use in the above transfer methods, and a method of making a pseudocapsid.

The invention also aims to provide a pharmaceutical composition comprising the pseudocapsid of the invention and a pharmacologically acceptable carrier.

According to the invention there is provided a method of transferring material into a host cell comprising providing a pseudocapsid formed from papovavirus major capsid antigen and excluding minor capsid antigens, which pseudocapsid has exogenous material associated therewith; and treating the host cell with the pseudocapsid so that the material is taken up by the cell and is biologically functional in that cell.

By "pseudocapsid" we mean a structure in which the only papovavirus capsid antigen is the major capsid antigen without minor capsid antigens, which structure is hollow so that it can contain exogenous material.

The term "papovavirus" defines a general family of viruses including polyoma virus (a mouse, virus), simian virus 40 (SV40), human variants (such as BK and JC) and papillomaviruses including human and bovine variants and other members. In each case, there is a major capsid antigen and one or more minor capsid antigens. For example, in papillomavirus the major antigen is L1 and the minor antigen is L2. In the present invention, the "pseudocapsids" are formed from the major capsid antigen and not the minor antigen(s).

The term "major capsid antigen" includes conservative variants thereof capable of assembling into a pseudocapsid and preferably having an antigenic determinant in common with the wild type antigen. The capsid antigen can be a hybrid of polyomavirus major capsid antigens, for example a hybrid of human BK virus major capsid antigen and mouse polyoma virus VP1.

By the exogenous material being "associated with" the pseudocapsid, we mean that the material is protected thereby. For example, exogenous DNA will be protected from degradation by DNases such as DNaseI, and exogenous protein will be protected from proteases. The exogenous material can be enclosed within an empty pseudocapsid or otherwise wrapped up with the capsid antigen.

The inventors have demonstrated that a simplified carrier consisting of a pseudocapsid involving only the major papovaviral capsid antigen can package and protect exogenous DNA, and transfer it into cells in a manner that allows for functional expression. A well-characterised gene, an efficiently transforming mutant form of the mouse polyoma virus middle T-antigen (MT), designated dl8MT (Griffin and Maddock, 1979), was chosen to show the worth of this system. The dl8-derived antigen possesses distinct physical and biological properties, which allow it to be easily assayed and distinguished from any wild type viral gene product that might have inadvertently contaminated recipient cells.

Papovaviruses have a broad host range and permissive cells include mammalian cells, such as rodent and human cells (Ponten, 1971). The pseudocapsids of the invention share this broad host range and can therefore be utilised in the transfer of exogenous material to a wide variety of cells.

The inventors have demonstrated that the pseudocapsids can successfully transfer exogenous genetic material in human cells.

Preferred host cells include mammalian cells, in particular rodents such as mice and rats, and human cells. Especially preferred human cells for in vivo gene transfer in accordance with the invention are lung cells.

Physical, non-viral gene transfer methods such as chemical and mechanical techniques and membrane fusion-mediated transfer via liposomes have been recently reviewed and assessed (Morgan and Anderson, 1993). The pseudocapsid (in the preferred embodiment involving genetic material) approach of the present invention resembles these procedures in that only the DNA intended for study, and no unwanted viral information, is introduced into cells. Moreover, the efficiency of functional gene transfer achieved by the method of the invention has been found to be between fifty and a hundred times greater than that achieved using conventional transfection methods.

The present data show that, in contrast to the calcium phosphate—or liposome-mediated route, long-term stable gene transfer and expression can be accomplished using pseudocapsids. Finally, it should be noted that whereas greater quantities of exogenous DNA are introduced into recipient rodent cells by the calcium phosphate technique, the latter route produces greater heterogencity in the delivered DNA than observed with the pseudocapsid approach, and is no more effective in terms of protein expression. The pseudocapsid approach is also advantageous in that it can be manipulated in a manner not applicable to chemical and physical transfer routes, making it of considerable value in future work including studies applied to gene therapy. The ease with which pseudocapsids can be produced and their efficient delivery of exogenous material, including the delivery of DNA to the cell nucleus, makes the present papovavirus pseudocapsid method of delivery especially attractive for use in therapy, especially gene therapy and antibody or drug targeting. A particular advantage of the pseudocapsid method of transfer is that it can deliver functional exogenous material to the nucleus of a cell.

In a further aspect the invention provides a pseudocapsid formed from papovavirus major capsid antigen and excluding minor capsid antigens, which pseudocapsid has exogenous material associated therewith, but excluding pseudocapsids associated with exogenous genetic material when the pseudocapsid is formed from only the mouse polyoma virus major capsid antigen, VP1. However, the invention does include pseudocapsids formed from mouse polyoma virus VP1 antigen if the exogenous genetic material and other exogenous material such as protein is associated with a pseudocapsid formed from only the mouse polyoma virus VP1 antigen.

In another aspect the invention provides a method of making a pseudocapsid comprising providing an empty pseudocapsid formed from papovavirus major capsid antigen and excluding minor capsid antigens; providing exogenous material; and mixing the empty pseudocapsid and exogenous material whereby the exogenous material becomes associated with the empty pseudocapsid. However, the invention does not include a method of making a pseudocapsid in which exogenous genetic material on its own is associated with an empty pseudocapsid formed from only the mouse polyoma virus major capsid antigen, VP1.

It should be noted that the invention does include a method of making a pseudocapsid in which both exogenous genetic material and other exogenous material such as protein is associated with a pseudocapsid formed from only the mouse polyoma virus VP1 antigen.

The term "exogenous material" as used herein means material other than wild type papovavirus nucleic acid. Preferably, the material is genetic material, for example DNA.

Preferably, the exogenous material is derived from an eukaryotic source, in particular from a mammal such as a rodent or a human. By material "derived from" we include material actually derived from a eukaryotic source, or obtained using eukaryotic material (for example cDNA obtained using eukaryotic mRNA) or synthesised to correspond to eukaryotic material (for example a chemically synthesised or recombinant copy of a eukaryotic cDNA, or an antisense oligonucleotide to eukaryotic genetic material).

Alternatively or additionally, the exogenous material may be a protein or other polypeptide, or any pharmacologically active compound, especially one which acts in or on the nucleus of cells.

In a preferred embodiment the exogenous material comprises a complex of two or more substances such as biological macromolecules. For example, if the sequence of the site to which DNA is to be targeted is known, this can be incorporated into the exogenous DNA together with the gene of interest, to promote homologous recombination at that site, using either double-stranded or single-stranded DNAs 20–200 bases long for this purpose. To promote the recombination event, single stranded recombinase binding proteins, such as the *Escherichia coli* RecA (B. J. Rao and C. M. Radding, Proc. Natl. Acad. Sci. U.S.A 91, 6161–6165, 1994) or its counterpart from *S. Cerevisiae*, Rad51, (A. Shinohara, H. Ogawa and T. Ogawa. Cell 69, 457 470, 1992) can be attached to DNA. Such a method can be used to greatly increase the efficiency and specificity of DNA integration into the host cell genome.

To demonstrate the effectiveness of the above method, for example, the dl8MT transforming gene of polyoma virus, to which a 20–200 long segment of mouse DNA has been ligated, with or without attached recombinase (or its active polypeptide site) can be incorporated into pseudocapsids and the ability of this carrier to produce dense foci, a marker of cellular transformation, monitored in vitro. For the mouse DNA sequence the results of D. M. Ding, M. D. Jones, A. Leigh-Brown and B. E. Griffin. EMBO. J. 1, 461–466, 1982; C. H. Streuli, N. S. Krauzewicz and B. E. Griffin, J. Virol. 64, 3570–3580 (1990) can be used. The comparative numbers of dense foci obtained are a marker of efficiency of the system and the effect produced by adding, for example, a recombinase protein. Sequence data obtained from chromosomal DNA from foci confirms the efficiency and specificity of the targeting. The present invention thus provides a method for specific targeting of exogenous DNA into a host chromosome.

A particularly preferred exogenous material for association with pseudocapsids of the invention comprises peptide-nucleic-acids (PNAs).

Peptide nucleic acids (PNAs) are single chain compounds consisting of a polyamide backbone having purine or pyrimidine bases attached to side chains, to form a base sequence superficially similar to that of a single chain nucleic-acid. Their structure, composition and synthesis is described by Nielsen, et al (1991), Science, 254, 1497–5001; Egholm et al (1992), American Chem. Soc, 114; and Cherny et al (1993), Proc. Natl. Acad. Sci. USA, 90, 1667–70.

PNAs are preferred exogenous material because they have properties that make them useful in therapy of diseases or to modify the structure of the genome of living cells by affecting gene expression.

In living cells, by binding one strand of complementary DNA in a duplex, and thereby displacing a portion of the other strand to form a D loop structure, PNAs can inhibit transcription of a gene, or cause DNA breakage as a consequence of the cellular enzymatic machinery attempting to repair the damage. Such breakage is a focus for an increased level of recombination with any homologous DNA strands present in the same pseudocapsid or delivered separately in another pseudocapsid. Such breakage can also kill the organism to which the DNA belongs. The organism either is the cell itself, or a protozoan parasite or a virus, etc. Since it is possible to synthesise unique PNA moieties having sequence specificities specific for pathogens such as viruses, including those like the retroviruses which may integrate their DNA into the genome of the host, PNAs can be used to selectively attack the target pathogen without any deleterious effect on the host genome.

Particularly preferred proteins or polypeptides are antibodies, recombinant antibodies, or fragments thereof.

The variable heavy ($V_H$) and variable light ($V_L$) domains of the antibody are involved in antigen recognition, a fact recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) *Proc. Natl. Acad. Sci.* USA 81, 6851–6855).

That antigenic specificity is conferred by variable domains and is independent of the constant domains is known from experiments involving the bacterial expression of antibody fragments, all containing one or more variable domains. These molecules include Fab like molecules (Better et al (1988) *Science* 240, 1041); Fv molecules (Skerra et al (1988) *Science* 240, (1038), single-chain Fv (ScFv) molecules where the $V_H$ and $V_L$ partner domains are linked via a flexible oligopeptide (Bird et al (1988) *Science* 242, 423; Huston et al (1988) *Proc. Natl. Acad. Sci.* USA 85, 5879) and single domain antibodies (dAbs) comprising isolated V domains (Ward et al, (1989) *Nature* 341, p44). A general review of the techniques involved in the synthesis of antibody fragments which retain their specific binding sites is to be found in Winter & Milstein (1991) *Nature* 349, 293–299.

By "ScFv molecules" we mean molecules wherein the $V_H$ and $V_L$ partner domains are linked via a flexible oligopeptide.

The advantage of using antibody fragments, rather than whole antibodies, are several-fold. The smaller size of the fragments may lead to improved pharmacological properties, such as better penetration of solid tissue. Effector functions of whole antibodies, such as complement binding, are removed. Fab, Fv, ScFv and dAb antibody fragments can all be expressed in and secreted from *E. coli*, thus allowing the facile production of large amounts of the said fragments.

Whole antibodies, and $F(ab')_2$ fragments are "bivalent". By "bivalent" we mean that the said antibodies and $F(ab')_2$ fragments have two antigen combining sites. In contrast, Fab, Fv, ScFv and dAb fragments are monovalent, having only one antigen combining site.

In a further aspect the invention provides a pharmaceutical composition comprising a pseudocapsid formed from a papovavirus major capsid antigen and excluding minor capsid antigens, which pseudocapsid has a pharmacologically active compound associated therewith; the pseudocapsid being provided together with a pharmacologically acceptable carrier.

Preferably, the pharmacologically active compound is a chemotherapeutic agent.

Chemotherapeutic agents are used to eliminate cancerous tissue. Recently, agents in the form of proteins and other biological products including molecules of the immune system such as tumour necrosis factor, interleukins, interferons and monoclonal antibodies have been used for chemotherapy.

As discussed by Jain, R. K. (Scientific American July 1994: 42–49), to eradicate tumours chemotherapeutic agents must disperse throughout the growths in sufficiently high concentrations. However, it has been found that tumours are resistant to such dispersal. Conventional chemotherapeutic agents are small (molecular weight lower than 2000 daltons) and when administered to a mammal, leave the blood vessels and migrate through normal tissue mainly by diffusion. However, the above biological products are larger molecules (molecular weight above 5000 daltons) and travel mainly by convection, that is, transport in a stream of flowing fluid.

Convection—dependent agents are inhibited from dispersing through the tumour because the uniform pressure in the tumour's interior prevents convection from operating. This may explain why such agents display disappointing tumour eradication results in vivo.

Both large and small chemotherapeutic agents are susceptible to degradation before they reach their target cancer cells. Repeated dosage is therefore required to maintain the sufficiently high concentrations needed for tumour eradication. This is expensive and may produce an immune response that degrades the agent before it has the chance to work.

Other tumour barriers which reduce the effectiveness of chemotherapeutic agents include the lack of oxygen in tumours which may cause them to secrete large amounts of lactic acid. Many agents are broken down or fail to work in an acidic environment.

A current strategy for overcoming the above problem is to link an enzyme with an antibody specific for a tumour cell antigen to form an "abzyme". The enzyme is capable of converting a prodrug into an active form capable of killing a tumour cell. Large amounts of the abzyme are injected in the blood stream so that it can accumulate in the tumour. The prodrug is injected once the abzyme has cleared from normal tissues. As the prodrug is small it can diffuse into the tumour and be activated by the abzyme to kill cancer cells.

However, this strategy is not wholly effective because the prodrug can be degraded quickly and can seep back into vessels and be cleared away from tumours just as easily as it can diffuse out of blood vessels.

The pseudocapsid approach for delivering chemotherapeutic agents is advantageous because it protects the agents from degradation, during transport to target cancer cells.

Preferably, the exogenous material comprises all or a coding part of at least one gene. Advantageously, expression of the gene in the host cell has a therapeutic effect on the cell and/or a multi-cellular organism comprising that cell. Genes of particular interest are given in the following table:

| DISEASES CAUSED BY SINGLE GENE DEFECTS: CURRENT TARGETS FOR GENE THERAPY ||
| --- | --- |
| Disease | Defective gene |
| Immunodeficiency | Adenosine deaminase |
|  | Purine nucleoside phosphorylase |
| Hypercholesterolaemia | LDL receptor |
| Haemophilia | Factor IX |
|  | Factor VIII |
| Gaucher's disease | Glucocerebrosidase |
| Mucopolysaccharidosis | β-glucuronidase |
| Emphysema | α-antitrypsin |
| Cystic fibrosis | Cystic fibrosis transmembrane regulator |
| Phenylketonuria | Phenylalanine hydroxylase |
| Hyperammonaemia | Ornithine transcarbamylase |
| Citrullinaemia | Arginosuccinate synthetase |
| Muscular dystrophy | Dystrophin |
| Thalassaemia | β-globin |
| Sickle cell anaemia | β-globin |
| Leukocyte adhesion deficiency | CD-18 |

This list indicates the principal current targets for gene therapy. Many of the diseases listed can be caused by defects in more than one gene; the gene defect listed is the defect targeted by current research.

If the exogenous material is protein it is protected from degradation by a protease. If the exogenous material is a pharmacologically active compound, it is protected from degradation caused by the surrounding environment.

The protection of exogenous material by the pseudocapsid from degradation can be determined readily. For example, to establish the levels of protection for DNA, the pseudocapsids can be packed with a radioactively labelled fragment, the buffer adjusted to 10 mM $MgCl_2$ and then exposed for 20 min at 37° C. to DNase I (100 µg/ml). The DNase treated sample is then fractionated on a 10–40% sucrose gradient made in buffer A (see below) lacking glycerol to separate protected from digested DNA. The refractive index and radioactivity of collected fractions is measured. Most radioactivity is unincorporated DNA and is found on the top of gradient. Radioactive peaks banding within gradients corresponding to pseudocapsids (as shown by electron microscopy) indicate that the labelled DNA and pseudocapsids are associated and affording protection to the DNA. The amount of protected DNA typically represents 2–5% of total DNA measured.

Exogenous material may be packaged, that is, incorporated into an empty pseudocapsid. By "empty" we mean that the pseudocapsid does not contain any papovavirus genetic material. It may of course contain other material, such as protein.

The attachment of protected exogenous material to the pseudocapsid, for example by coating with charged molecules, is a preferred method of associating the material with the empty pseudocapsid because it enables larger amounts of material to be transferred.

For example, larger fragments of exogenous genetic material can be packaged using an in vitro method such as that described below, and then further protected by the addition of charged molecules (such as poly-L-lysine or basic histones), followed by incubation for 30 mins. at 37° C.

Binding charged molecules causes exogenous genetic material such as DNA to alter its' conformation which affects the amount of genetic material that can be packaged into empty pseudocapsids.

The pseudocapsids used may be provided in the form of an icosahedron, like the wild type papovavirus capsid, or larger spherical or filamentous shapes which are advantageous because they permit packaging of larger nucleic acid fragments. The term "pseudocapsid" is thus not limited to particles which closely resemble wild type papovavirus capsids.

The transfer of larger amounts of exogenous material may be desirable. For example transfer of larger fragments of genetic material is advantageous because there appears to be a size constraint on the amount of genetic material that can be packaged and transferred to host cells, using the empty icosahedral VP1 pseudocapsids, for example. The wild type viral genome of papovaviruses is 5.2 kbp and, using the passive DNA packaging procedures of Barr et al. (1979) or Slilaty et al. (1982), the amount of DNA that can be packaged is around 3 kbp. Whereas this size would be adequate for expression of many mammalian cDNAs, or, for example, oligonucleotides to be used for antisense "knockout" experiments (ie where a gene function is deleted), it would preclude packaging of a number of mammalian genes in their entirety.

Recombinant baculoviruses carrying genes for papovaviruses major capsid antigen, such as the mouse polyoma virus major capsid antigen VP1, have been constructed and the antigens can be expressed in insect cells as described by Forstová et al. 1993. In this method insect cells are infected with a recombinant baculovirus expressing VP1, harvested 72 hours post infection, resuspended in buffer A (50 mM NaCl, 10 mM Tris-HCl, pH 7.4. 0.01 mM $CaCl_2$, 0.01% Triton X-100) and disrupted by sonication.

Cell debris is removed by low speed centrifugation and VP1 pseudocapsids purified on a CsCl density gradient. Peak fractions of pseudocapsids are subjected to centrifugation through a sucrose gradient (10–40%) and peak fractions (monitored by immunoblotting and electron microscopy) are then concentrated by CsCl gradient centrifugation. After each centrifugation the pseudocapsids are dialysed into buffer A.

In a preferred method, Sf9 insect cells are incubated at a multiplicity of infection of 10–20 with a recombinant baculovirus expressing VP1, harvested 72 hrs postinfection, resuspended in buffer A (150 mM NaCl, 10 micromolar $CaCl_2$, 10 mM Tris-HCl, pH 7.6, 5% glycerol, 0.01%, Triton X-100) and disrupted by sonication. Cell debris is removed by low speed centrifugation at 8000xg. The empty VP1 pseudocapsids in the supernatant are concentrated by pelleting through a sucrose cushion and then by banding on a CsCl gradient. The fractions containing purified empty pseudocapsids, as revealed by refraction index measurements or electron microscopy, are dialysed into buffer A.

Using the above methods the yield of empty VP1 pseudocapsids is at least ten times greater than that achieved when the same procedure is carried out by co-infection of insect cells with recombinant baculoviruses expressing VP1, and the minor capsid antigens VP2 and VP3. Furthermore, empty VP1 pseudocapsids are just as efficient as VP1, VP2 and VP3 capsids at packaging exogenous genetic material.

Empty pseudocapsids formed from other papovavirus major capsid antigens can be produced using similar methods.

Protecting the exogenous material with an empty pseudocapsid is conveniently achieved for exogenous DNA, for example, by mixing 1 μg DNA with 10–60 μg of empty pseudocapsids and incubating the mixture in 150 mM NaCl, 0.01 mM $CaCl_2$ 10 mM Tris, at pH 7.4. 0.01% TX-100, for 10 minutes at 37° C. The mixture is then subjected to osmotic shock by quick dilution with water to a final concentration of 35 mM $NaCl_2$ with incubation for an additional 20 minutes. The pseudocapsids incorporating exogenous DNA can then be used in the exogenous material transfer method of the invention.

Exogenous material, in the form of protein and polypeptides such as antibodies and fragments thereof, and pharmacologically active compounds, can be packaged inside an empty pseudocapsid by a similar procedure in which the DNA is substituted in the above method by the exogenous material to be packaged.

Alternatively, exogenous material is associated with empty pseudocapsids by dissociating the empty pseudocapsid structure and reassembling it in the presence of the material.

An advantage of the pseudocapsids of the invention is that they are easier to produce than capsids containing both major and minor capsid antigens. This is because it is difficult to control the proportions of the various capsid antigens in the assembled capsid. Consequently, the properties of the capsids produced will vary and this unpredictability is undesirable.

A further advantage of the present pseudocapsids for in vivo exogenous material transfer over known capsids is that they are less likely to evoke a strong immune response than capsids because they only contain a single foreign antigen, the major capsid antigen.

Treatment of host cell with pseudocapsids in accordance with the invention can be carried out by washing the cells in serum free medium and incubating them with pseudocapsids diluted to 1 ml/$10^6$ cells with tissue culture medium. Following 90 mins incubation, medium containing serum is added to the culture. For example, 15 μg of pseudocapsids containing an agarose gel-purified fragment (2.5 μg) of the cellular gene p43 (Koch et al., 1990) under the control of the cytomegalovirus immediate early promoter can be used to treat human embryo lung (HEL) fibroblast cells, using $2 \times 10^2$ cells. The cells are then incubated at 37° C. for 72 hours post treatment.

To test for functioning of the p43 fragment, cells are harvested by washing with phosphate buffered saline (PBS), and lysing in Laemmli sample buffer (Laemmli, 1970). Proteins are fractionated on 10% SDS-PAGE, immunoblotted and probed initially with a p43 specific monoclonal antibody, then anti-β tubulin antibody (Sigma). Immune complexes are detected with an HRP conjugated secondary antibody (Dako plc) and chemiluminescent ECL reagent (Amersham plc).

DESCRIPTION OF THE DRAWINGS

FIG. 1(A) Schematic presentation of the polyoma virus DNA fragment incorporated into pseudocapsids. The linear BclI-EcoRI (1680 b.p.) DNA fragment from pPyMTdl8, containing the polyoma virus origin of replication (ori), promoter (p) and the gene for the middle T antigen dl8 deletion mutant (as noted below), was gel purified before use in DNA packaging and transfection experiments. Polyoma virus sequence numberings are those of Soeda et al. (1980). Cleavage sites for restriction enzymes are noted.

FIG. 2 Morphology and soft agar assay of cell lines cloned from foci of transformed cells, phase contrast microscopy of;

FIG. 3 Analysis of expression of the dl8 middle T antigen (Dl8MT) gene in transformed cell lines.

In FIGS. 3(A) and 3(B), the gels contain protein from: (tracks 1), the cloned cell line, C1, derived from calcium phosphate transfection; (tracks 2 and 3), cell lines P1 and P2 from pseudocapsid treated cells; (tracks 4), the parental rat-2 line; and, (tracks 5), rat-2 cells transformed with mutant dl8 polyoma virions. The location of the dl8MT (and LT, where observed) is noted, as are molecular size markers (at right).

FIG. 4 Southern blot analysis of transformed cell lines. Tracks contain: (a, e and i), DNA from cell line C1 (see above), generated by calcium phosphate precipitation, cleaved with HindIII (no site in viral DNA), with PstI (one site) and with SacI (two sites), respectively; (tracks b, l and j), and (c, g and k), DNA from two of the individual transformed foci generated with polyoma pseudocapsids, cleaved respectively with HindIII, PstI and SacI; tracks (d, h and l), DNA from control rat-2 cells cleaved with the same enzymes; track m, the BclI-EcoRI input fragment (1 ng). Higher molecular weight bands probably reflect integrated viral DNA. The location of the 654 bp internal SacI fragment of the MT gene indicative of the efficiency of exogenous DNA, (FIG. 1A) is noted (•). Migration positions of molecular weight markers (in kb) are indicated.

Preferred embodiments of the invention will now be described, by way of example only, with reference to the above figures.

EXAMPLE 1

Preparation of VL-VP1 Recombinant Baculoviruses and Isolation of Polyoma Virus VP1 Empty Pseudocapsid Particles

*Escherichia coli*, strain DH5, was used for the propagation of transfer vectors and recombinant plasmids. Where a digestion with the BclI enzyme was used, plasmids were propagated in *E. coli* JM110 strain (a dam dcm mutant derivative of JM 101) (Yanish-Perron et al., 1985, Gene 33: 103–119).

The baculovirus transfer vectors p VL 941 containing a Bam HI cloning site, and p VL 1393 containing a multiple cloning site polylinker were used for the construction of recombinant plasmids where polyoma VP1 was placed under control of the polyhedron promoter. Plasmid pMJA2 containing the whole polyoma virus genome inserted into the EcoRI site (Krauzewicz et al., 1990) was used for isolation of the gene.

The recombinant plasmid pVL-VP1 was constructed by ligation of the EcoRV-XbaI 1584 b.p. fragment of the pMJA2 plasmid (polyoma virus numberings 4106 EcoRV to 2522-XbaI are those of Soeda et al., (1980) with vector pVL1393, cleaved with SmaI and XbaI. Competent bacteria, DH5, were transformed with ligation mixture and plasmid pVL VP1 was selected.

*Spodoptera frugiperda* (Sf9) cells were grown as monolayer cultures at 27° C. in standard TNM-FH medium containing 10% foetal calf-serum (FCS), as described by Hink (1970, Nature: 226: 466–467). *Autographa californica* nuclear polyhedrosis virus (AcNPV) was propagated as described by Summers (1987, Texas agricultural Bulletin No. 1555, Texas agricultural Experiment Station). A recombinant baculovirus containing polyoma VP1, was prepared by in vivo allelic exchange between wild type AcNPV DNA and the individual DNA of recombinant transfer plasmid pVL-VP1, according to the method described previously (Forstova et al., 1989). Sf9 cells were infected with 10 plaque forming units per cell of recombinant baculovirus. A monolayer of cells was washed with TNM-FH medium and the inoculum of virus was added. Cells were rocked at room temperature for 1 hr. Complete medium with 10% FCS was then added and cells were incubated at 27° C.

Isolation of empty polyoma virus pseudocapsids from insect cells. Insect cells were infected with VL-VP1 baculovirus. Cells were harvested 72 p.i., resuspended in buffer A (10 mM Tris-HCl [pH 7.6], 150 mM NaCl, 10 micromolar $CaCl_2$ 5% glycerol, 0.01% Triton X-100), and disrupted by sonication (10 amplitude microns [MSE Soniprep 150] for 3 secs). Cell debris was removed by centrifugation (20 min. 8,000×g) and particles purified by centrifugation though a sucrose cushion (20%, made in buffer A lacking glycerol), centrifuged at 150000×g for 3 hours. The pellet was resuspended in buffer A, lacking glycerol and sonicated briefly.

CsCl was added to a density of 1.30–1.33 g/ml and the gradient formed by centrifugation for 20 hours at 150000×g. Peak fractions of densities between 1.30 and 1.35 g/ml were collected and dialysed overnight against buffer A.

Electron microscopy Formvar (EMSCOPE)-coated grids were incubated for several seconds with 10-µl pseudocapsid samples, drained of surplus liquid, transferred to a drop of 3% phosphotungstic acid (pH 6.6), and left for 45 s. The grids were dried and stored at room temperature.

EXAMPLE 2

Packaging of Polyoma Virus dl8 MT Gene into VP1 Pseudocapsids

Cells: The dl8 virion transformed line, as control, was isolated from foci formed following infection of rat-2 cells with the dl8 mutant virus. Both these cells and the parental rat-2 cell line were passaged in complete Dulbecco's modified Eagle's medium (DMEM) containing 10% foetal calf serum.

The intron of the gene for polyoma virus middle T antigen was deleted by site directed mutagenesis (see FIG. 6 and Strauss et al., 1986). A BclI/EcoRI linear DNA fragment was packaged into pseudocapsids according to the procedure of Barr et al. (1979): briefly, 1 µg agarose gel-purified DNA was mixed with 10–60 µg of empty pseudocapsids and incubated in 150 mM NaCl, 10 micro M $CaCl_2$, 10 mM Tris, pH 7.6, 5% glycerol, 0.01% Triton X-100 for 10 min. at 37° C. The mixture was then exposed to osmotic shock by quick dilution with water to a final concentration of 35 mM NaCl and incubation was continued for an additional 20 min. After this, aliquots of particles to be used for transfer into cells were subjected to DNase treatment and gradient purification. To establish the level of DNA protected by the particles, the packaging mixture was adjusted to 10 mM $MgCl_2$ and exposed to DNaseI (100 µg/ml) for 20 minutes at 30° C. An excess of calf thymus DNA and EDTA to 50 mM was added, and packaged DNA was released from the pseudocapsids in the presence of 100 mM dithiothreitol, 50 mM EDTA and 1% w/v SDS. It was deproteinised by phenol:chloroform (24:1) extraction and loaded onto an agarose gel. The amount of input DNA fragment was identified by Southern blotting using a $^{32}$P-radiolabelled BclI-EcoRI fragment.

Figure 1A:
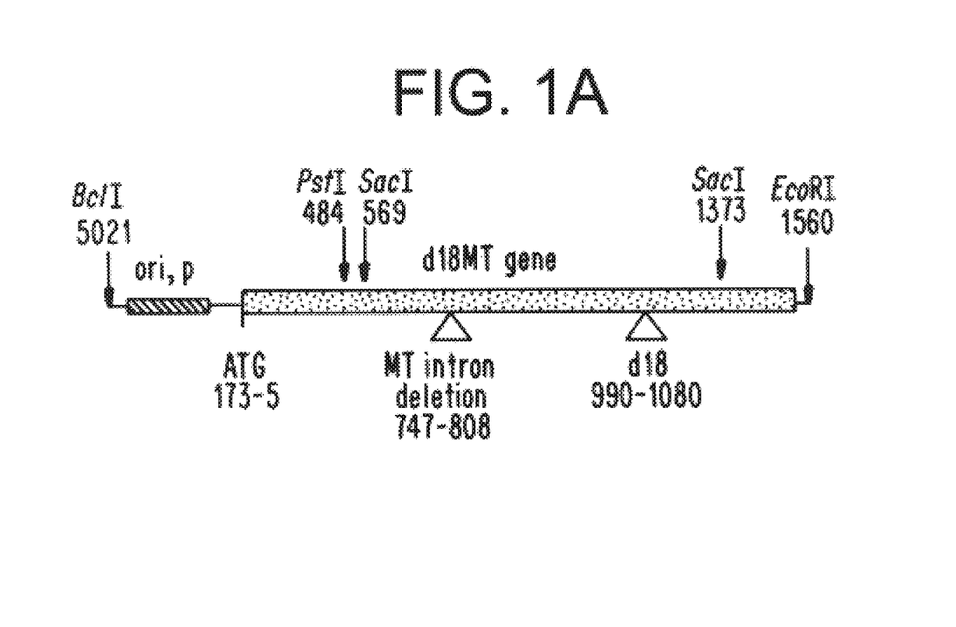
Figure 1B:
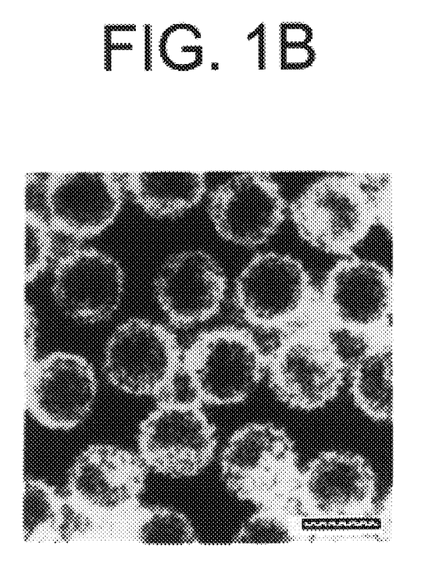
FIG. 1(B) Electron microscopy of self-assembled icosahedral VP1-pseudocapsids isolated from insect cells. Bar= 50 nm.
Figure 1C:
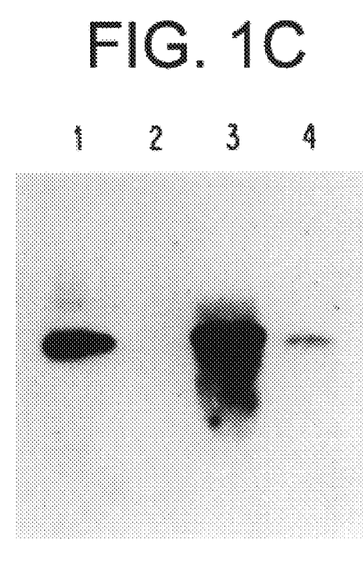
FIG. 1(C) Protection of packaged DNA by pseudocapsids from DNaseI cleavage. The tracks contain; 1 and 2, control reactions with 1 μg DNA, in the absence of pseudocapsids, without and with DNaseI treatment, respectively; 3 and 4, packaging mixture with 1 μg DNA, without and with DNaseI treatment, respectively.
Figure 2A:
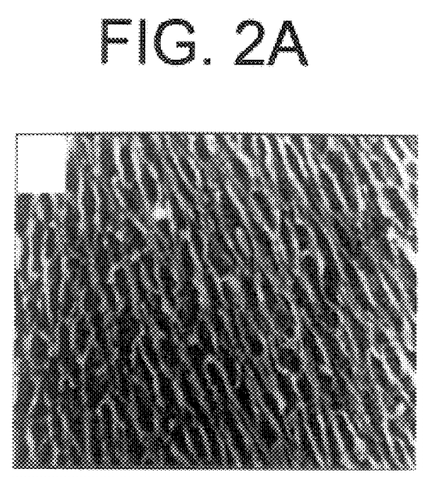
FIG. 2(a) the parental untreated rat-2 cell line.
Figure 2B:
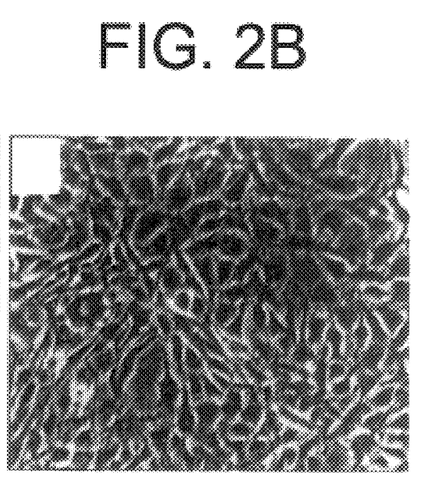
FIG. 2(b) an example of a transformed cell line obtained from a focus formed following calcium-phosphate transfection.
Figure 2C:
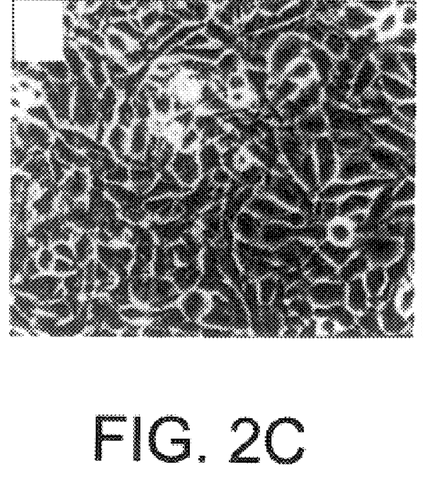
FIG. 2(c) cells isolated from a dense focus derived from pseudocapsids packaged with dl8MT DNA.
Figure 2D:
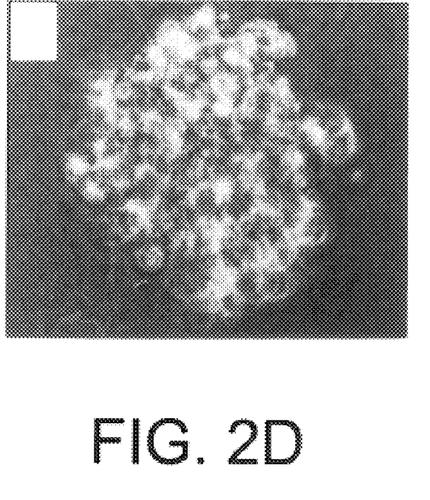
FIG. 2(d) shows a transformed colony from a pseudocapsid derived cell line growth in soft agar.

Data with regard to packaging are given in FIG. 1. FIG. 1A contains a schematic diagram of the linear DNA fragment used in transfer in our initial studies and FIG. 1B shows an electron micrograph of the purified icosahedral VP1 particles utilised. The DNA was packaged into the particles by a previously described procedure, where viral empty capsids obtained during the course of a lytic polyoma virus infection were used (Barr et al., 1979). FIG. 1C shows a Southern blot of total input DNA (tracks 1 and 3) compared with that remaining after treatment of the packaging mixture with DNase I in the absence (track 2) or presence (track 4) of the pseudocapsids. About 2–5% of the input DNA was found to be incorporated as DNaseI-resistant material into VP1 pseudocapsids (compare tracks 3 and 4, FIG. 1C). In a complementary study (not shown), where radiolabelled DNA was packaged into pseudocapsids, about 5% of the radioactivity was found to co-sediment with the particles on sucrose density gradient centrifugation.

EXAMPLE 2(i)

Dissociation/Reassociation Packaging of Exogenous Material

An alternative packaging method is to dissociate the capsids in the presence of an ion chelator, such as EGTA, and a reducing agent, such as beta-mercaptoethanol. (The concentrations of each chemical being calculated by titration for each capsid preparation.) The pseudocapsids are then reassociated, in the presence of the material being packaged, by dialysis against buffer A using a calcium ion concentration titrated for against the particular pseudocapsid preparation. Packaged material and particles can then be separated from unpackaged material by centrifugation through a 10–30% sucrose gradient (made in buffer A, lacking glycerol) at 150000×g for 3 h.

EXAMPLE 3

Cellular Response to Introduced Exogenous DNA

Following an encapsidation step, the packaging mixture was used to introduce DNA into recipient rat immortalized (rat-2) cell using a normal polyoma virus infection protocol. Three quarter confluent cell sheets were washed once in culture medium, DMEM, lacking serum, and pseudocapsids, (diluted to 1 ml/$10^6$ cells with DMEM) were added. The cells were incubated at 37° C. for 90 min and then supplemented with 4 ml DMEM+10% foetal calf serum. Cells were left in culture to observe whether dense foci, a marker of MT expression and cellular transformation, would develop. Control experiments were performed on rat-2 cells using the same amount of DNA employed in the initial packaging step either in mock infection (in the absence of pseudocapsids) or in co-precipitation with calcium phosphate in a classical transfection procedure (Graham and van der Eb, 1973). In these experiments, dense foci of cells were visible after three weeks in all but the mock-infected cultures. Foci were either counted after staining or taken from the plate for propagation in culture. The data, given in Table 1, are results from two experiments. They show that the numbers of foci obtained with pseudocapsids considerably exceed those from the calcium phosphate transfection. If the relatively low efficiency of the packaging step (see FIG. 1C) is taken into consideration, in assessing the numbers of dense cell foci produced in the respective experiments, the pseudocapsid route of DNA introduction was found to be 50–100 fold more effective than the transfection procedure for delivering functionally useful DNA to the cells.

TABLE 1

Comparison of Efficiency of Formation of Dense Foci.

| Method of DNA transfer | No. of foci per dish | Efficiency of transfer (foci/microgram DNA) |
| --- | --- | --- |
| Absorption of "naked" DNA | 0 | 0 |
| Calcium phosphate transfection | 15 | 7.5 |
| Pseudocapsid transfer | 57 | 570* |

*Calculation based on packaging efficiency of 5%.

Individual foci, picked from the transformation assays and established in monolayer culture, were compared morphologically with the initial rat-2 cultures and assessed for their ability to grow as colonies in semi-solid media, another marker of cellular transformation. FIG. 2 shows the morphology of the normal (mock infected) rat fibroblast cells (FIG. 2a) compared with those of a typical transformed cell culture established from foci selected from calcium phosphate transfected (FIG. 2b) or pseudocapsid treated cells (FIG. 2c), as well as typical colony growth observed in soft agar culture (FIG. 2d) using cells shown in FIG. 2c. The formation of transformed colonies suggested that the dl8MT gene packaged into VP1 particles produced by the recombinant virus had been stably introduced into the rat-2 cells, and is apparently functionally active.

Figure 3A:
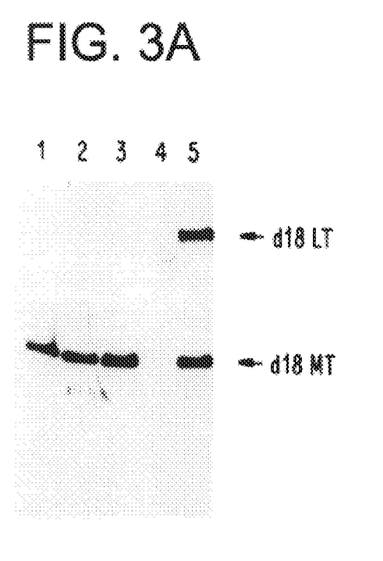
FIG. 3(A) Immunoblot of cell lysates probed with PAb 701, a monoclonal antibody specific for the N-terminal region of the three polyoma virus early antigens.

To demonstrate that the latter was the case, rather than, for example, transformants having arisen spontaneously, protein samples were analysed for the presence and expression of the viral antigen. Two assays were used to examine the MT in these cell lines, one involving immuno (Western) blotting, and the other examining the well-characterized interaction between MT and the cellular oncogene, c-src (Courtneidge and Smith, 1983), using a standard protein kinase assay (Collett and Erikson, 1978). The Western blot data (FIG. 3A) show that dl8MT—which migrates by SDS-gel electrophoresis faster than wild type MT, due to a deletion in the gene—was expressed in either transfected or pseudocapsid-treated rat-2 cells, and that the levels of expression are high (tracks 1–3) when compared with that found in equal numbers of dl8 virion-derived transformed cell line (track 5). (In the latter case, the large T antigen, which cannot be expressed off the recombinant dl8 MT cDNA shown in FIG. 1a, is also observed, as was the viral small T-antigen, not shown.)

Figure 3B:
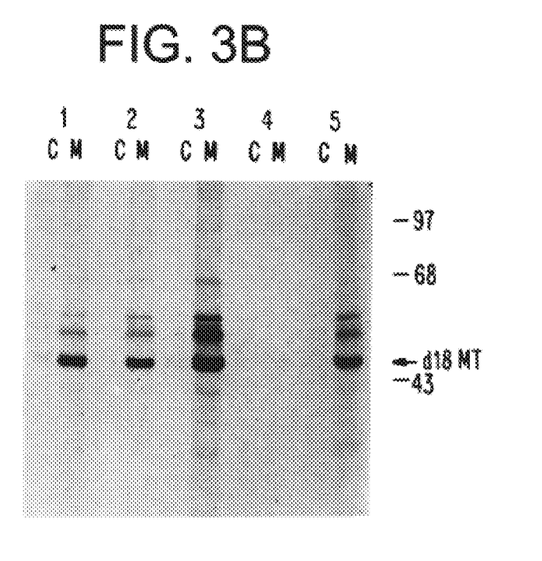
FIG. 3(B) In vitro kinase reaction of immunoprecipitates of cell lysates using Pab701, which does not recognise MT complexed to c-src (C-tracks) or Pab721, a monoclonal antibody which precipitates protein kinase active complexes of MT and c src (M-tracks).

Similar data (not given) were obtained from the other foci-derived cell lines. The results obtained from an in vitro kinase assay (FIG. 3B) are consistent with those from focus formation and soft agar assays. They demonstrate that the MT produced after pseudocapsid treatment of cells is able to interact with, and activate, the product of the cellular src oncogene in a manner indistinguishable from MT produced in virally-infected cells (Smith et al., 1979; Courtneidge and Smith, 1983), and thus appears to be fully functional. No MT activity was observed in the rat-2 parental cells.

State of Exogenous DNA in Host Cells

Figure 4:
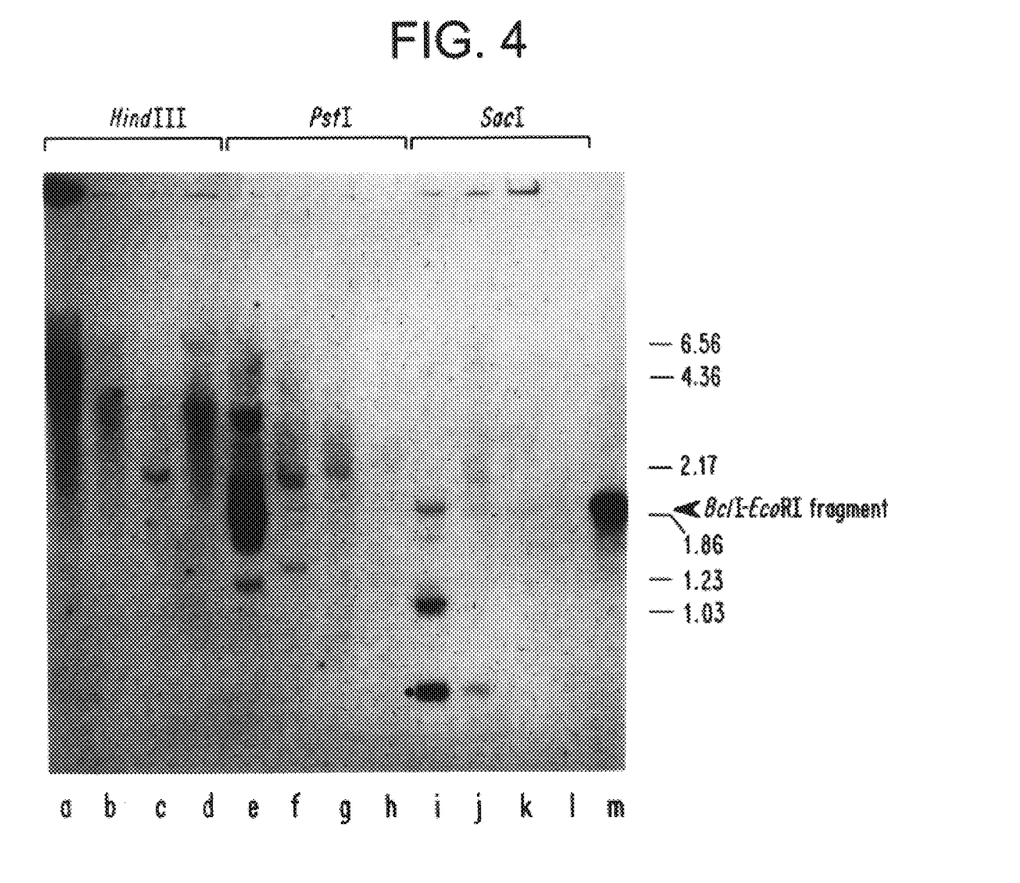
Figure 5:
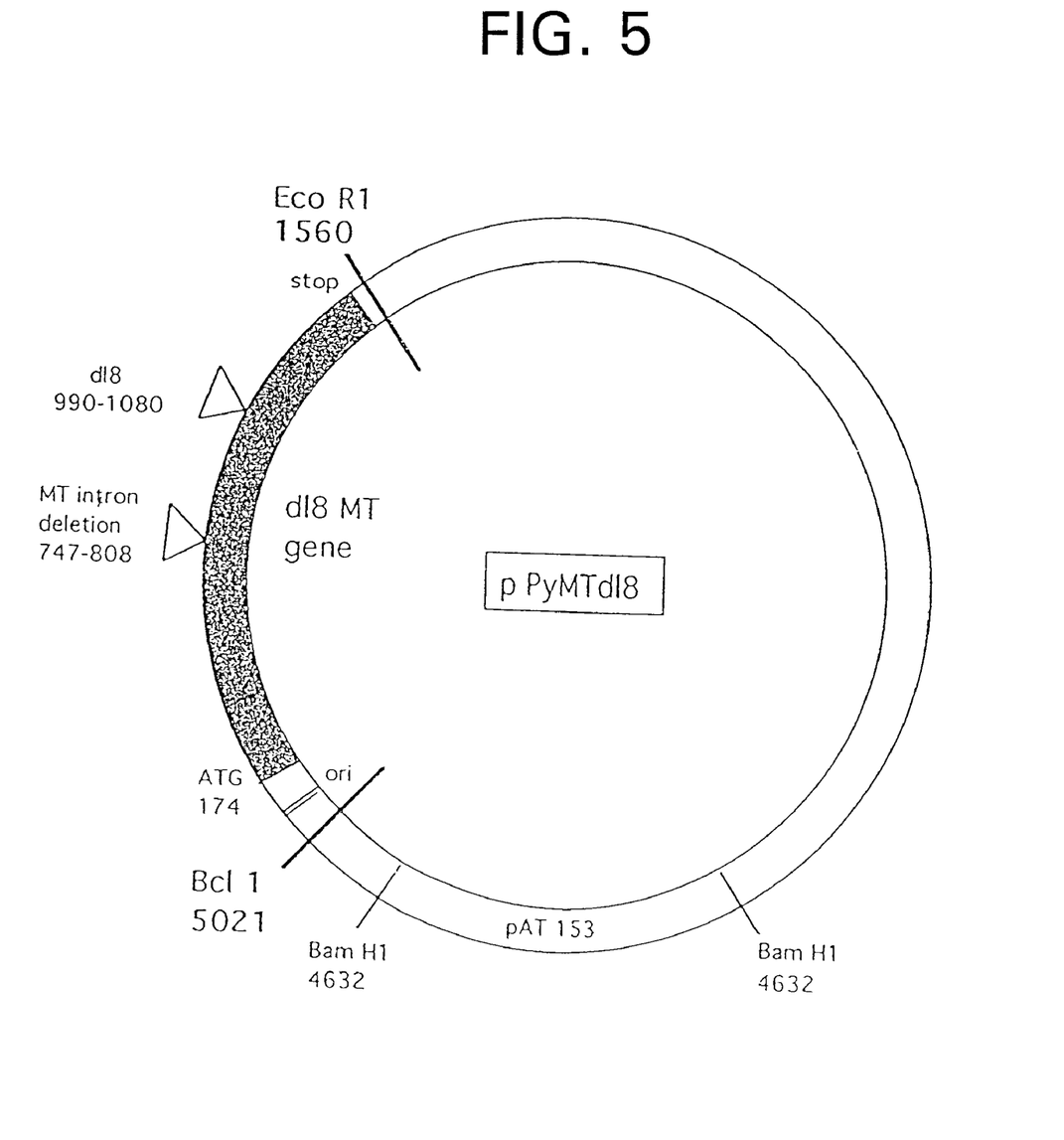
FIG. 5 A schematic map of the plasmid pPyMTdl8 containing the genome of the polyoma dl8 mutant virus.

After showing efficient and biologically active expression of the dl8MT gene from DNA transported into cells via pseudocapsids, the inventors examined the state of the exogenous DNA in the cell, with particular regard to whether or not it had been integrated into the host chromosome. Southern blot analyses of total cellular DNA from early passages of two lines of cells derived from pseudocapsid transfer, and one from calcium phosphate transfection, were thus carried out, alongside the corresponding DNA from the parental (rat-2) cells. The data obtained are presented in FIG. 4. Here it can be seen that calcium phosphate transfected cultures contain high copy numbers of non-(or tandemly)-integrated dl8 DNA, as illustrated (tracks a, c and i), whereas much lower levels, if any, of these forms of DNA are observed in the experiments where the polyoma VP1 pseudocapsids were used for gene transfer (tracks b, e, f, g, j and k). In the latter case, bands are present on the gels that probably reflect single copy integration into the host chromosome suggesting that the incoming DNA is incorporated into the host genome probably at one, or a few sites only. To assess this further, DNA was cleaved with appropriate restriction enzymes (see FIG. 1A). Digestion with SacI resulted in the release of an internal 654 bp viral fragment. This band is clearly evident in DNA from the calcium phosphate transfected cells, and visible on longer exposures in lines generated from the VP1 pseudocapsid transfer (FIG. 4, tracks i–k), suggesting that the incorporated viral DNA has not undergone gross rearrangement. These data also demonstrate that the high level of dl8MT expression observed (FIG. 3) cannot be linearly related to copy numbers of the incorporated DNA since cells derived from the calcium phosphate precipitation technique (tracks a, e and i) contain multiple copies of the introduced gene, whereas pseudocapsid transfer results only in low level or single integration events (tracks b, c, f, g, j and k).

EXAMPLE 4

Comparison of DNA Carrier Systems

Semi-confluent 25 cm$^2$ T-flasks of rat-2 immortalized cells were either mock infected by exposure to 1 $\mu$g of the "naked" BclI-EcoRI linear DNA fragment containing the gene polyoma MT, or transfected with 1 $\mu$g of this fragment using calcium phosphate, or treated with 60 $\mu$g of pseudocapsids mixed with 1 $\mu$g DNA, respectively. Media on cultures were changed weekly. At the end of three weeks, foci of transformed cells were either visualized for counting with Leishmann's staining solution or selected as individual foci for propagation. Cell lines from four foci (P1–4) obtained from pseudocapsid DNA transfer and from two foci (C1–2) isolated from calcium phosphate transfected cells were established in short-term culture. Individual isolated cell lines were analysed for their morphological appearance and their ability to grow as transformed cells in soft agar (Türler and Beard, 1985).

Protein Analysis

For Western immunoblot detection, proteins from total cell lysates were separated by SDS-PAGE (Laemmli, 1970), electroblotted and probed with monoclonal antibodies to polyoma virus early antigens (Dilworth and Griffin, 1982). Immunocomplexes were detected with a horseradish peroxidase conjugated secondary antibody (Dako plc) and visualised with ECL reagent (Amersham plc). Kinase assays were performed on immunoprecipitates with radiolabelled [$^{32}$P]-γ ATP (Collett and Erikson, 1978; Dilworth, 1982) using antibodies Pab 701 and 721. Gels were exposed to autoradiographic film (XAR-5. KODAK) for four hours at −70° C.

Southern Blotting Analyses

Restriction enzyme digests of 20 μg total cellular DNA were separated on a 0.8% agarose gel, blotted and hybridised with $^{32}$P-labelled BclI-EcoRI DNA fragment. The filter was exposed to autoradiographic film (XAR-5, KODAK) for four days at 70° C.

EXAMPLE 5

Introduction of Heterologous DNA Into Human Cells

To investigate whether papovavirus pseudocapsid carrier procedure could be adapted for human cells, the inventors sought to enhance the expression of an endogenous function, p43, found at low levels in normal cells (Koch et al., 1990), by gene transfer into human embryo lung (HEL) fibroblasts. HEL cells, derived from primary human embryo lungs, had been passaged (weekly) about 30 times in culture. An agarose gel-purified NruI/EcoRI restriction fragment (2.5 μg) of the cellular gene, p43 (Koch et al., 1990), cloned into pcDNA3 (Promega Inc) under the control of the cytomegalovirus immediate early promoter was packaged into VP1 pseudocapsids (15 μg) as described above. The packaged mixture, prepared in duplicate, was used to treat human embryo lung (HEL) fibroblast cells, using 2×10$^3$ cells. As a control, cells were also treated with equivalent quantities of "naked" DNA, empty pseudocapsids, or with DNA transfected using the calcium phosphate co-precipitation technique. Cells were harvested 72 hr. later by washing with phosphate buffered saline (PBS), and lysing in Laemmli sample buffer (Laemmli, 1970). Proteins were fractionated by 10% SDS-PAGE, immunoblotted and probed initially with a p43 specific monoclonal antibody, as above, then anti-β tubulin antibody (Sigma). Immuno complexes were detected with an HRP conjugated secondary antibody (Dako, plc) and chemiluminescent ECL reagent (Amersham plc). The results obtained from duplicate experiments show a small (several-fold) but significant increase in gene expression in HEL cells treated with the pseudocapsids as compared with that observed in mock or control experiments (cells treated with naked DNA or pseudocapsids only. Co-precipitation of the p43 gene with calcium phosphate caused no increase in expression over basal level p43 expression. To establish the validity of these findings, the levels of tubulin in the experiments was assessed on the same gel. Significant differences were not observed in the quantities of tubulin seen in individual tracks when an anti-tubulin antibody was used.

The results demonstrate that papovavirus pseudocapsids can be used as carriers for introducing biologically functional exogenous DNA stably into recipient cells. The pseudocapsids do not appear toxic to cells, in that little cell death was observed during the course of the experiments, even though immunofluorescence data (not shown) demonstrated high levels of pseudocapsid in many cells. In a comparison made with the calcium phosphate co-precipitation transfection method, the pseudocapsid carrier approach was found to be both more selective and more efficient. This may reflect either greater efficiency of DNA uptake, enhanced protection of DNA, more effective transport to nuclei, preferential integration into host chromosomes, or a combination of two or more of these factors.

These results show that at least transient up regulation of expression of the product of a human gene, p43 (Koch et al., 1990), can be obtained in HEL cells when it is introduced by pseudocapsids. Thus, carrier papovavirus pseudocapsids have application in human cells. It is noteworthy that companion experiments using DNA co-precipitated with calcium phosphate (Graham and van der Eb, 1973) were not equally successful. Documentation in the past has noted the difficulties of transfecting "foreign" material into human cells (Hoeijmakers, et al. 1987; Mayne et al., 1988). The corresponding success of the pseudocapsid carrier approach may rely on the fact that efficient targeting to the cell nucleus occurs by this procedure.

Increasing the Amount of Genetic Material Incorporated in VP1 Pseudocapsid

There is probably a size constraint on the amount of genetic information that might be packed within VP1 icosahedral pseudocapsids, and the upper limit for studies such as those performed here may be determined by the size (5.2 kbp) of the polyoma wild type viral genomes. Using the passive polyoma packaging procedure of Barr et al., (1979) or Slilaty et al., (1982), using "naked" DNA, the limit appears nearer to 3 kbp. Whereas this size would be adequate for expression of many mammalian cDNAs, or oligonucleotides to be used for antisense "knockout" experiments, or other small biologically active molecules, it would preclude packaging of a number of genes in their entirely.

EXAMPLE 6

Associating Pseudocapsids and DNA

The following technique can be used to increase the size of the DNA fragment or other exogenous material, which can be transferred to host cells by pseudocapsids. The technique involves packaging the DNA into empty pseudocapsids as described in Example 2 and then further protecting the DNA by incubation at 37° C. for 20 mins in the presence of 10 μg polylysine (pL300)/60 μg pseudocapsids.

EXAMPLE 7

An alternative approach is to precondense DNA with a binding protein prior to packaging.

EXAMPLE 8

Larger Pseudocapsids

An alternative approach to allow larger amounts of exogenous material such as DNA fragments to be transferred to host cells by pseudocapsids, takes advantage of the observation that not all the baculovirus expressed papovavirus major capsid antigen such as VP1 self-assembles into standard 45 nm icosahedral structures. Rather, some of the capsid antigen produced assembles into much larger spherical and filamentous shapes (Forstová et al., 1993). Similar morphological findings were reported earlier where, with polyoma virus infected cells, electron microscopic examination revealed capsids ranging in size from 27 to 65 nm (Eddy, 1969). In the present invention, the larger of these assemblies are isolated and used to package DNA as described in Examples 1 and 2. These larger pseudocapsids can package and transfer much larger DNA fragments than the standard sized icosahedral structures.

EXAMPLE 9

Formation of Pseudocapsids From HPV L1 Protein

Pseudocapsids may be formed from human papillomavirus L1 protein by the method of Hagensee et al (1993) *J. Virol.* 67, 311–322. Briefly, the HPV L1 gene (from HPV type 1 in this case) is inserted into a vaccinia virus by the TK recombination method and expressed in suitable cells, for example BSC-1 monkey kidney cells. Similarly, L1 can be expressed from a recombinant baculovirus.

Purification of HPV-1 capsids: BSC 1 cells (20- to 150-mm plates) were infected with recombinant vaccinia virus at a multiplicity of infection of 30. Cells were incubated at 37° C. for 72 hr in Dulbecco's modified Eagle's medium supplemented with 5% fetal bovine serum and antibiotics. Cells were then collected by aspiration. Cells were pelleted by centrifugation (1,000×g, 10 min) and washed once with phosphate-buffered saline (PBS). A nuclear fraction was prepared by resuspending the cell pellets in 10 ml of HEPES [N-2-hydroxyethylpiperazine-N'2-ethanesulfonic acid] buffer (10 mM HEPES [pH 7.9], 10 mM KCl, 1.5 mM $MgCl_2$) and incubating on ice for 10 min. Cells were lysed by homogenization, 50 strokes with a tight-fitting pestle. Nuclei were collected by centrifugation at 2.000×g for 10 min. The nuclei were resuspended in 2 ml of PBS and sonicated for 2 min, and 2.1 g of cesium chloride was added. The nuclear suspension was placed into ultracentrifuge tubes, and the density was adjusted to 1.340 g/ml. Samples were spun at 45,000 rpm for 36 hr at 4° C. in an SW55 rotor. Fractions were collected by puncturing the bottom of the tube or by needle aspiration of the capsid band. Density of the resultant fractions was determined with a Bausch & Lomb refractometer. Fractions were dialyzed against three changes of PBS, and HPV proteins were detected PBS', by Western blot. Fractions containing L1 proteins were analyzed for pseudocapsid formation by electron microscopy. The yield was approximately $10^{10}$ particles.

To determine whether the L1 proteins could self-assemble to form pseudocapsids, cells infected with the recombinant vaccinia virus were collected and nuclei were isolated, lysed, and layered onto cesium chloride gradients. After centrifugation for 48 hr, fractions were collected and analyzed for L1 protein by Western blot.

A large amount of L1 protein migrating at a density of approximately 1.30 g/ml was produced. When analyzed by electron microscopy, 55-nm icosahedral particles were found.

The empty pseudocapsids were associated with the exogenous material, for example a mammalian cDNA, by the osmotic shock and re-assembly techniques described above.

EXAMPLE 10

Association of Empty Pseudocapsids and Other Exogenous Material

Non-genetic exogenous material such as proteins and polypeptides such as antibodies or fragments thereof, and pharmacologically active compounds, can be associated with empty pseudocapsids using the method described for exogenous DNA in example 2. The method is simply modified by substituting the exogenous material for the DNA.

It is preferred that the exogenous material is one which acts in or on the nucleus of a cell such as a nucleoside analogue. The pseudocapsids of the invention deliver material efficiently to the cell nucleus. For example, the pseudocapsids can be used to deliver hormones to the cell nucleus to trigger the action of nuclear signaling molecules which activate hormone responsive elements to control gene expression.

EXAMPLE 11

Administration of Pseudocapsids to Mammals

The aforementioned pseudocapsids of the invention may be administered by any conventional method including oral and parenteral (eg subcutaneous or intramuscular) injection. A preferred method of administration is by means of a nasal inhalation spray, in which the pseudocapsids are produced as in an aerosol. Such an approach has been used in the gene therapy of cystic fibrosis as an effective way of deliverying the therapeutic agent to lung epithelial cells. The treatment may consist of a single dose or a plurality of doses over a period of time.

Whilst it is possible for a pseudocapsid of the invention to be administered alone, it is preferable to present it as a pharmaceutical formulation, together with one or more acceptable carriers. The carrier(s) must be "acceptable" in the sense of being compatible with the pseudocapsid of the invention and not deleterious to the recipient thereof. Typically, the carriers will be water or saline which will be sterile and pyrogen free.

EXAMPLE 12

Pharmaceutical Formulations of the Pseudocapsid

The formulations may conveniently be presented in unit dosage form and may be prepared by any of the methods well known in the art of pharmacy. Such methods include the step of bringing into association the active ingredient (pseudocapsid of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (eg povidone, gelatin, hydroxypropylmethyl cellulose), lubricant, inert diluent, preservative, disintegrate (eg sodium starch glycollate, cross-linked povidone, cross-linked sodium in carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide a desired release profile.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use.

Extemporaneous injection solutions and suspensions may be prepared from sterile powders, granules and tablets of the kind previously described.

Preferred unit dosage formulations are those containing a daily dose or unit, daily sub-dose or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

References

ANDERSON, W. F. Human gene therapy, (1992). *Science* 256, 808–813.

BARR, S. M., KECK, K. & APOSHIAN, H. V. (1979). Cell-free assembly of a polyoma like particle from empty capsid and DNA. *Virology* 96, 656–659.

COLLETT, M. S. & ERIKSON, R. L. (1978) Protein kinase activity associated with the avian sarcoma virus src gene product. *Proc. Natl. Acad. Sci. USA* 75. 2021–2024.

COURTNEIDGE, S. A. & SMITH, A. E. (1983). Polyoma virus transforming protein associates with the product of the c-src cellular gene. *Nature* 303, 4135 139.

DILWORTH, S. M. (1982). Protein kinase activities associated with distinct antigenic forms of polyoma virus middle T-antigen. *EMBO J.* 1, 1319–1328.

DILWORTH, S. M. & GRIFFIN, B. E. (1982). Monoclonal antibodies against polyoma virus tumor antigens. *Proc. Natl. Acad. Sci.* U.S.A. 79, 1059–1063.

EDDY, B. E. (1969). In, *Virology Monographs* (1969). 7, Springer-Verlag (Vienna, N.Y.) pp. 1–112.

FORSTOVÁ, J., KRAUZEWICZ, N., WALLACE, S., STREET, A. J., DILWORTH, S. M., BEARD. S. & GRIFFIN, B. E. (1993). Cooperation of structural proteins during late events in the life cycle of polyomavirus. *J. Virol.* 67, 1405–1413.

GRAHAM, F. L. & VAN DER EB, A. (1973). Transformation of rat cells by DNA of human adenovirus 5. *Virology* 54, 536–539.

GRIFFIN, B. E. & MADDOCK, C. (1979). New classes of viable deletion mutants in the early region of polyoma virus. *J. Virol.* 31, 645–656.

HOEIJMAKERS, J. H. J., ODIJK, H. & WESTERVELD, A. (1987). Differences between rodent and human cell lines in the amount of integrated DNA after transfection. *Exp. Cell Res.* 169, 111–119.

KOCH, I., HOFSCHNEIDER, P. H., LOTTSPEICH, F., ECKERSKORN, C. & KOSHY, R. (1990). Tumour-related expression of a translation elongation factor like protein. *Oncogene* 5, 839–843.

LAEMMLI, U. K. (1970). Cleavage of structural proteins during the assembly of the head of bacteriophage T4. *Nature* 227, 680–685.

MAYNE, L. V., JONES, T., DEAN, S. W., HARCOURT, S. A., LOWE, J. E., PRIESTLEY, A,. STEINGRIMSDOTTIR, H., SYKES, H., GREEN. M. H. L. & LEHMANN, A. R. (1988) SV40-transformed normal and DNA-repair-deficient human fibroblasts can be transfected with high frequency but retain only limited amounts of integrated DNA. *Gene* 66, 65–76.

MONTROSS, L., WATKINS, S., MORELAND, R. B., MAMON, H., CASPAR, D. L. D. & GARCEA, R. (1991). Nuclear assembly of polyomavirus capsids in insect cells expressing the major capsid protein VP1. *J. Virol.* 65, 4991–4998.

MORGAN, R. A. & ANDERSON, W. F (1993). *Ann. Rev. Biochem.* 62, 191–217.

MULLIGAN, R. C. (1993). The basic science of gene therapy. *Science* 260, 926–932 (1993).

PONTÉN. J. (1971). *Virology monographs* 8, pp. 46–92 (Springer Verlag, Wien).

SLILATY, S. N. and APOSHIAN, H. V. (1983). *Science*, 220, 725–727.

SLILATY, S. N., BERNS, K. I. and APOSHIAN, H. V. (1982) *J. Biol. Chem.* 257: 6671–6675.

SMITH, A. F., SMITH, R., GRIFFIN, B. & FRIED, M. (1979). Protein kinase activity associated with polyoma virus middle T antigen in vitro. *Cell*, 18, 915–924.

STRAUSS, M. M., STREULI, C. H. & GRIFFIN, B. E. Efficient oligodeoxyribonucleotide-directed deletion mutagenesis using pEMBL vectors: removal of early region introns from polyoma virus mutants. *Gene* 49, 331–340 (1996).

STRAUSS, M., HERING,. S., LUBBE, L. & GRIFFIN, B. E. (1990). Immortalisation and transformation of human fibroblasts by regulated expression of polyoma virus T antigens. *Oncogene* 5, 1223–1229.

SOEDA, E., ARRAND, J. R., SMOLAR, N., WALSH, J. E. & GRIFFIN, B. E. (1990). Coding potential and regulatory signals of the polyoma virus genome. *Nature* 283, 445–453.

TÜRLER, H & BEARD, P. (1985). Simian virus 40 and polyoma virus: growth, titration, transformation and purification of viral components. In *"Virology: A practical approach"* (ed. Mahy, B. W. J.) pp. 169–192 (IRL press, Oxford).

WAGNER, E., ZATLOUKAL, K., COTTEN, M., KIRLAPPOS, H., MECHTLER, K., CURIEL, D. T. & BIRNSTIEL, M. L. (1992). Coupling of adenovirus to transferrin-polylysin/DNA complexes greatly enhances receptor-mediated gene delivery and expression of transfected genes. *Proc. Natl. Acad. Sci. U.S.A.* 89, 699–103.

What is claimed is:

1. A method of transferring material into a host cell comprising:

providing a pseudocapsid formed from a papovavirus major capsid antigen and excluding minor capsid antigens, which pseudocapsid has exogenous material associated therewith, but excluding a method in which exogenous material is associated with an empty pseudocapsid formed from only the mouse polyoma virus major capsid antigen, VP1; and treating the host cell with the pseudocapsid so that the material is taken up by the cell and is biologically functional in that cell.

2. The method as claimed in claim 1 wherein the biological functioning of the exogenous material in the host cell has a therapeutic effect on a multi-cellular organism containing that cell.

3. The method as claimed in claim 2 wherein the multi-cellular organism is a mammal.

4. The method as claimed in claim 3 wherein the mammal is a human.

5. The method as claimed in claim 3 wherein the pseudocapsid is administered to the mammal together with a pharmacologically acceptable carrier.

6. A pseudocapsid formed from papovavirus major capsid antigen and excluding minor capsid antigens, which pseudocapsid has exogenous material associated therewith; but excluding pseudocapsids associated with exogenous genetic material and no other exogenous material when the pseudocapsid is formed from only the mouse polyoma virus major capsid antigen VP1.

7. The pseudocapsid as claimed in claim 6 wherein the major capsid antigen is from a virus selected from the group consisting of human papilloma virus, human polyoma virus, mouse polyoma virus, bovine papilloma virus, and simian virus 40.

8. The pseudocapsid as claimed in claim 6 wherein the exogenous material is genetic material.

9. The pseudocapsid as claimed in claim 8 wherein the genetic material comprises all or a coding part of at least one gene.

10. The pseudocapsid as claimed in claim 6 wherein the exogenous material is a peptide nucleic acid.

11. The method as claimed in claim 1 wherein the pseudocapsid is provided by packaging the material inside an empty pseudocapsid.

12. The method as claimed in claim 1 wherein the material is associated with the pseudocapsid by attaching it to the pseudocapsid.

13. The method as claimed in claim 1 wherein the mixture of empty pseudocapsid and exogenous material is subjected to osmotic shock.

14. The method as claimed in claim 1 wherein the empty pseudocapsid and exogenous genetic material are mixed in the presence of calcium ions.

15. The method as claimed in claim 1 wherein the pseudocapsid is formed from the major capsid antigen of a virus selected from the group consisting of human papilloma virus, human polyoma virus, mouse polyoma virus, bovine papilloma virus, and simian virus 40.

16. The method as claimed in claim 1 wherein the host cell is treated in vitro.

17. The pseudocapsid formed from papovavirus major capsid antigen and excluding minor capsid antigens, which pseudocapsid has exogenous material associated therewith, wherein the pseudocapsid transfers the exogenous material into a host cell so that the material is taken up by the cell and is biologically functional in the cell; but excluding pseudocapsids associated with exogenous genetic material and no other exogenous material when the pseudocapsid is formed from only the mouse polyoma virus major capsid antigen VP1.

18. The pseudocapsid as claimed in claim 17 wherein the exogenous material is genetic material.

19. A pseudocapsid as claimed in claim 17 wherein the pseudocapsid is formed from the major capsid antigen of a papovavirus selected from the group consisting of human papilloma virus, human polyoma virus, mouse polyoma virus, bovine papilloma virus, and simian virus 40.

* * * * *